United States Patent [19]

Suzuki et al.

[11] Patent Number: 4,945,039
[45] Date of Patent: Jul. 31, 1990

[54] STANDARD MATERIALS FOR MEASUREMENT OF IMMUNE COMPLEXES AND METHOD FOR MEASUREMENT OF IMMUNE COMPLEXES

[75] Inventors: Hideaki Suzuki, Koganei; Kenji Hosoda, Kawagoe; Takaharu Kubota, Hino; Yuji Fukumoto, Hachioji, all of Japan

[73] Assignee: Teijin Limited, Osaka, Japan

[21] Appl. No.: 60,957

[22] Filed: Jun. 10, 1987

Related U.S. Application Data

[63] Continuation of Ser. No. 711,134, Mar. 13, 1985, abandoned.

[30] Foreign Application Priority Data

Mar. 13, 1984 [JP] Japan ................................. 59-46422

[51] Int. Cl.$^5$ ........................................... G01N 33/564
[52] U.S. Cl. ........................................... 435/7; 435/18; 435/188; 436/501; 436/507; 436/512; 436/518; 436/821; 530/390; 530/391
[58] Field of Search ................... 530/390, 391; 436/8, 436/501, 512, 513, 518, 821, 546, 507; 435/7, 18, 88

[56] References Cited

U.S. PATENT DOCUMENTS

| | | | |
|---|---|---|---|
| 4,235,869 | 11/1980 | Schwarzberg | 435/7 |
| 4,283,383 | 8/1981 | Masson et al. | 436/506 |
| 4,332,783 | 6/1982 | Pernice et al. | 436/541 |
| 4,595,655 | 6/1986 | Self | 436/518 |
| 4,661,347 | 7/1987 | Muller-Eberhard et al. | 530/390 |
| 4,686,181 | 8/1987 | Doná | 435/810 |

FOREIGN PATENT DOCUMENTS

81/02469 9/1981 PCT Int'l Appl. .
82/01593 5/1982 PCT Int'l Appl. .

OTHER PUBLICATIONS

Chem. Abst. 87:165807C of Nov. 21, 1977.
Chem. Abstract 91:54291T of Aug. 15, 1979.
L. F. Fries et al., *Journ. Exp. Med.*, 160, 1640-1655, 1984.
J. H. Kennedy et al., *Clin. Chem. Acta*, 70, 1-31, 1976.
A. B. Pereira et al., *Journ. Immunol.*, 125, 763-770, 1980.
Ngo et al., Febs Letters, 116, 285-288, 1980.

*Primary Examiner*—Esther M. Kepplinger
*Assistant Examiner*—David A. Saunders
*Attorney, Agent, or Firm*—Sughrue, Mion, Zinn, Macpeak & Seas

[57] ABSTRACT

A standard material for measuring immune complexes which is prepared by chemically binding immunoglobulin and/or its fragment with a complement and/or its derivative through the medium of a bifunctional reagent. By using the standard material, the standard curve which is used for measuring immune complexes existing in the blood is obtained.

10 Claims, 2 Drawing Sheets

STANDARD MATERIALS FOR MEASUREMENT OF IMMUNE COMPLEXES AND METHOD FOR MEASUREMENT OF IMMUNE COMPLEXES

This is a continuation of application Ser. No. 711,134 filed March 13, 1985, now abandoned.

BACKGROUND OF THE INVENTION

The present invention relates to the standard materials useful for the detection and measurement of immune complexes (or antigen-antibody complexes) existing in the blood, blood-plasma or other body fluids of a patient who is suffering from diseases arising from immune complexes and to the quantitative measurement of immune complexes by use of said standard material.

Immune complex diseases may be brought under two categories, i.e. such diseases resulting from endogenous autoantigen as chronic articular rheumatism, systemic lupus erythematosus (SLE), chronic glomerulonephritis, tumor, etc., and such diseases resulting from exogenous antigen as acute glomerulonephritis, leukemia, etc. The formation of immune complexes is one of the protective reactions which take place in a living body and they are ingested and destroyed by reticuloendothelial cells and other phagocyte immediately after their formation in the body of a person in normal health. Under abnormal conditions, however, where immune complexes are formed in large quantities due to continued antigenical stimulus or where they unyieldingly get beyond control of reticuloendothelial cells and phagocytes, the immune complexes remain in the blood, blood-plasma, or other body fluids to settle in the tissue of the human body and finally destruct the tissue. The determination of immune complexes in the blood, blood-plasma or body fluids is, therefore, to offer reliable information useful for making diagnosis of and trying remedies for diseases resulting from immune complexes. In view of such vital need for quantitative estimation of immune complexes existing in the blood or body fluids, various means are now put into practice, of which immunochemical assay has widely come into use because of its accurate determination and simple procedures.

In this immunochemical assay, immune complex is measured by use of a substance which is able to combine specifically with the component of immune complex, such as complement component, conglutinin (kg), anti-complementary antibody, Raji cell, rheumatoid factor (RF), and blood platelet, followed by comparison of the obtained result with the immune complex standard material of known concentration. Since it is impracticable to separate immune complexes which actually exist in the blood or body fluids for use in the assay, a similitude of immune complex which has characteristics immunologically similar to immune complex. As a similitude of immune complex to be used as a standard agent in the assay, a substance obtained by treating immunoglobulin with heat and chemicals to have it denatured and aggregated, such as aggregated human immunoglobulin (AHG) and a substance obtained by cross-linking immunoglobulin with the use of a bisudiazo compound and the like to have it denatured are presently used.

However, it is difficult to prepare these substances of good reproducibility and constant properties because of lack of uniformity in their properties including molecular weight. Moreover, they have another defect of having unsatisfactory shelf life stability which tends to form a precipitate or sediment, thus making it difficult to give an accurate concentration value when used in measurement. Since it is especially very difficult to obtain a similitude of immune complex having complement reactivity in case where human IgA is used for aggregation purpose as a standard material for use in measuring IgA immune complex, attempts have been made to have IgA and IgG aggreagatad together; however, much difficulty is still found in preparing standard agents of good uniformity and excellent reproducibility, thus constituting a barrier against an accurate measurement of IgA immune complex.

SUMMARY OF THE INVENTION

In view of such situation as mentioned above, the inventors of the present invention have conducted intensive researches on the development of a similitude of immune complex of uniform properties and stability, which can be prepared with comparative ease, for use as a standard material in the determination of immune complexes. The result is the finding that a substance, which is obtained by chemically binding complement components to immunoglobulins by means of a bifunctional reagent, possesses all qualification required of a standard material to be used in the determination of immune complexes, thus completing the present invention.

Accordingly the present invention is directed to (1) a standard material for measuring immune complexes which is prepared by chemically binding a complement and/or its derivative to immunoglobulin and/or its fragment by means of a bifunctional reagent and (2) a method of quantitatively measuring immune complexes in the blood or body fluids by use of an immune complex measuring standard curve prepared according to the technique of immunoassay wherein a solid phase carrier, which is fixed with anti-(human complement) antibody and/or its F(ab')$_2$ or conglutinin (kg), is allowed to come into contact with a solution of any of said immune complex measuring standard materials of known concentration, followed by the treatment with an enzymelabeled or radiolabeled anti-(human immunoglobulin) antibody

DESCRIPTION OF THE PREFERRED EMBODIMENTS

Figure 1:
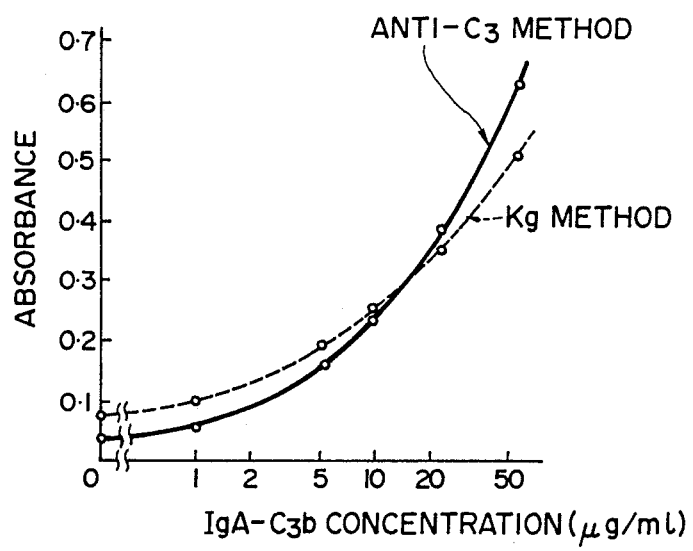
FIG. 1 presents standard curves prepared by use of IgA-C3b conjugates for determining immune complex of IgA type by enzyme immunoassay, showing a standard curve according to the anti-C3 method and one according to the conglutinin (kg) method.

Immunoglobulins used in the present invention are human immunoglobulins G, M, A, E, and D, each having its F(ab')$_2$, Fab', and Fc for its structural components. As complements, C1, C2, C3, C4, C5, C6, C7, C8, and C9 are used and C3 is used desirably. As derivatives of complements, their structural components such as C1q, C1v, C1s, C3b, C3c, C3d, etc. may be mentioned, and C3b may be a desirable one. As other derivatives, there are substances obtained by chemically forming an SH group in complements or introducing the group thereinto. For instance, a substance resulting from fission of the thiol ester group in a C3 molecule caused by treating C3 with monomethylamine or the like, and a substance obtained by allowing N-succinimidyl pyridyl-dithiocarboxylate to react with a complement, followed by reduction to introduce an SH group into its molecule may be mentioned.

As the bifunctional reagent to be used in this invention, such dialdehyde compounds as glutaraldehyde, etc., such diisocyanate compounds as toluene-2,4-diisocyanate, diphenylmethane-4-,4'-diisocyanate, etc., such diepoxy compounds as ethylene glycol diglycidyl ether, glycerol diglycidyl ether, etc., such bisdiazo compounds as bis (4-azidophenyl)sulphone, bis-(4-azidophenyl)methane, etc., such carbodiimide compounds as 1-ethyl-3-(3-dimethyoxyaminopropyl)carbodiimide, N,N'-dicyclohexyl carbodiimide, 1-cyclohexyl-3-(2-morpholinyl-4-ethyl)carbodiimide methyl-p-toluenesulfonate, etc., such N-succinimidyl N-maleimidocarboxylates, N-succinimidyl m-(N-maleimido)benzoate, N-succinimidyl p-(N-maleimidomethyl)benzoate, N-succinimidyl 4-(N-maleimidomethyl)cyclohexane-1-carboxylate, etc., and such N-succinimidyl pyridyldithio-carboxylates, N-succinimidyl 3-(2-pyridyldithio)propionate, etc. may be mentioned.

The abovementioned methods of preparing the standard materials for detecting and measuring immune complexes by use of immunoglobulins (immunoglobulins or their structural components), complements (complements or their derivatives) and bifunctional reagents can be carried out according to any discretionary techniques. For instance, a method wherein a mixture of a bifunctional reagent and a phosphate buffer solution containing immunoglobulins and complements is allowed to undergo the single-stage reaction and a method wherein firstly the reaction between either immunoglobulins or complements and bifunctional reagent added thereto in large excess is carried out, and the bifunctional reagent remaining reacted is separated and removed by dialysis or gel filtration, and then the other immunoglobulins or complements which are to form the conjugate are added to the reaction product to complete the multistage reaction may be mentioned. A preferable technique may propose to use such hetro bifunctional reagents as N-succinimidyl n-maleimido-carboxylates, N-succinimidyl, pyridyldithio-carboxylates etc. as said bifunctional reagents to allow any of them to act upon immunoglobulins or complements to react with the amino groups existing in their molecules. Thereafter, in case where immunoglobulins are used, a method is adopted to make complements, such as C3b, which have thiol groups in their molecules, react with the reaction product, or in case where complements are initially used, a method is taken to allow immunoglobulins, such as Fab', which have thiol groups in their molecules, to react with the reaction product.

Incidentally, as said immunoglobulins or complements which have thiol groups in their molecules, thiol group containing proteins can also be used. These proteins are obtained by allowing a N-succinimidyl pyridyldithio-carboxylate to react with proteins of these immunoglobulins or complements to introduce pyridyl-dithio groups into their molecules, followed by their reduction conducted under mild conditions to introduce thiol groups into them.

The reaction of immunoglobulins and/or complements with a bifunctional reagent can be carried out by adding a bifunctional reagent solution to a phosphate buffer solution containing any of these proteins and carrying out the reaction at a temperature of 0° to 50° C., preferably 4° to 40° C., for a period of 1 minute to 48 hours, preferably 30 minutes to 24 hours. In case where the reaction is conducted in two stages, the reaction between the protein bound with a bifunctional reagent and the protein which is to form a conjugate can be conducted at a temperature of 0° to 50° C., preferably 4° to 40° C., for a period of 6 to 72 hours, preferably 12 to 48 hours.

Preparation of a measuring standard curve by use of the standard materials for detecting and measuring immune complexes of this invention and the measurement of the immune complex in the blood or body fluids by use of said standard curve can be made following the procedures mentioned below.

In the first step, such complement-binding proteins as anti-(human complement antibody and/or its F(ab')$_2$, or conglutinin (Kg), are allowed to come into contact with such solid phase carriers as plastic microplates, plastic balls, plastic tubes, glass beads for EIA use in a phosphate buffer solution with cooling for more than 12 hours, thus making the complement-binding proteins fix onto the solid phase carriers. Then, the immune complex measuring standard material is disolved in a phosphate buffer or the like to make a dilute solution of known concentration and the solution is brought into contact with the solid phase carrier, to which a complement-binding protein is bound, at a temperature of 0° to 50° C., preferably 4° to 40° C., for a certain prescribed time within the range of 30 minutes to 24 hours, preferably 1 to 12 hours, to make the solution pick up the standard material from the carrier. A phosphate buffer solution of an enzymelabeled or radiolabeled anti-(human immunoglobulin) antibody is added thereto and the mixture is set to the reaction at a temperature of 0° to 50° C., preferably 4' to 40° C. for a certain prescribed time ranging from 30 minutes to 24 hours, preferably 1 to 12 hours, to combine the anti-(human immunoglobulin) antibody with the immunoglobulin component existing in the molecule of said standard material.

As the enzyme to be used for enzyme-labeling the anti-(human immunoglobulin) antibody, there are alkali phosphatase, $\beta$-D-galactosidase, horseradish peroxidase, etc. As the substances to be used for radiolabeling, there are $I^{125}$, $P^{32}$, and reagents which contain these substances in them. In case where enzymelabeled anti-(human immunoglobulins are used, the solid phase carrier is firstly washed and then an enzyme substrate and, if necessary, a color reagent or fluorescent reagent or luminescent reagent are added thereto to have it colored or make it fluorescent or luminescent. Thereafter, its absorbance, fluorescence intensity, and luminescence intensity are measured and these values and the concentration of the standard material are plotted to obtain a standard curve. As the substrates and reagents mentioned above, such colorimetric substrates as p-nitrophenol phosphate, etc. and such fluorescent substrates as 4-methylumbelliferyl phosphate, etc. are used in case of alkali phosphatase; such colorimetric substrates as 0-nitrophenol-$\beta$-D-galactoside, etc. and such fluorescent substrates as 4-methylumbelliferyl-$\beta$-D-galactoside, etc. in case of $\beta$-D-galactosidase; and such colorimetric reagents as 5-aminosalicylic acid, o-phenylenediamine, 2,2'-azinodi(3-ethylbenzthiazoline)-

6'-sulphonic acid, etc. together with substrate of hydrogen peroxide, such fluorescent reagents as p-hydroxyphenyl propionic acid, etc., and such luminescent reagents as luminol, etc. are used in case of horseradish peroxidase.

A single-stage reaction, in which a solid phase carrier bound with complement binding protein, standard agent, and enzyme- or radio-labeled anti-(human immunoglobulin) are allowed to react with each other at a time, can be conducted to make the measurement.

In the measurement of immune complexes existing in the blood or body fluids by using the standard curve thus prepared, the concentration of the material to be studied can be determined by comparing the value, which is detected and measured by use of the labeled material, with the standard curve, after the reaction is carried out according to the same procedure that is adopted in preparing the measuring standard curve, with the exception of the use of the material to be studied in the place of the standard material.

The standard materials for measuring immune complexes can be prepared as the ones having excellent stability and reproducibility and accordingly the measurement of immune complexes made by immunoassay with the use of these standard materials is a technique of high precision and excellent reproducibility.

The following examples and drawings illustrate the present invention more specifically. It should be understood that these examples and drawings are given to explain the invention and not limit the scope of the invention. "%" used in the examples indicates per cent by weight.

EXAMPLE 1

1.0 mg of human serum IgA was dissolved in 1 ml of 0.1M phosphate buffer of pH 7.5 containing 0.1M NaCl, and after 40 μl of 30 mM ethanol solution of N-succinimidyl 3-(2-pyridyldithio)propionate (SPDP) was added thereto at 30° C. with stirring, the mixture underwent the reaction for 1 hours. The reaction mixture was then subjected to chromatographic separation of the protein from the unreacted low molecular substances such as SPDP on a column (1×45 cm) of Sephadex G25 equilibrated with said phosphate buffer while making 0.8 ml fractions at the flow rate of 0.5 ml/min. to obtain the fractions containing the pyridylsulfurized human serum IgA. These fractions were pooled and concentrated to have the protein of 4 mg/ml concentration by use of a collodion bag while cooling with ice water. Thereafter, 0.25 ml of 0.1M phosphate buffer of pH 7.2 containing 1.0 mg of human C3b prepared according to the method proposed by J.O. Minta et al. (Journal of Immunology, vol. 118, p. 2192; 1977) was added to 0.25 ml of thus obtained concentrate of pyridylsulfurized human serum IgA. After the mixture was left standing at 4° C. for 24 hours, it was chromatographed on a column (1.5×45 cm) of ultragel ACA34 equilibrated with 0.1M phosphate buffer of pH 7.2 to obtain 1.0 ml fractions at the flow rate of 0.5 ml/min., thus separating the formed IgA-C3b conjugate from the unreacted proteins. The fractions containing IgA-C3b complex were then pooled.

The content of IgA which constitutes the conjugate in said solution of IgA-C3b conjugate was determined by the sandwich technique of enzymeimmunoassay with the use of the goat anti-human IgA antibody fixed solid phase carriers and the horseradish peroxidase labeled F(ab)2 fragment of goat anti-human IgA antibody (alpha hair specific)(manufactured by Cappel) and it was found that the yield of IgA-C3b conjugate based on the starting material of human serum IgA was 70%.

EXAMPLE 2

A solution of IgG-C3b conjugate was obtained by allowing human IgG to react with human C3b through the medium of SPDP according to the same method as Example 1 by use of human IgG in the place of human serum IgA which was used in Example 1. The content of IgG component which constituted the conjugate in the obtained solution was determined by the sandwich technique of enzyme immunoassay with the use of the solid phase carrier fixed with goat anti-(human IgG) antibody and horseradish peroxidase labeled F(ab)2 fragment of goat anti-human IgG antibody (gamma chain specific) (manufactured by Cappel) and it was found that the IgG-C3b conjugate was obtained in a 70% yield.

EXAMPLE 3

The reaction between IgM and human C3b was carried out by use of C3b in excess at the equivalence point in the presence of SPDP according to the same method as Example 1, wherein IgM was used in the place of human serum IgA which was used in Example 1. The reaction product was then passed through a column (1.5×45 cm) of ultragel ACA 44 equilibrated with 0.1M phosphate buffer of pH 7.2 to obtain 1.0 ml fractions at the flow rate of 0.5 ml/min., thereby separating the formed IgM-C3b conjugate from the substances remaining reactive. The fractions containing the IgM-C3b conjugate were pooled to give an IgM-C3b conjugate solution.

EXAMPLE 4

A solution was prepared by dissolving 1.0 mg of human C3 in 1 ml of 0.1M phosphate buffer (pH 7.5) containing 0.1M NaCl. 40 μl of 30 mM ethanol solution of N-succinimidyl 3-(2-pyridyldithio)propionate (SPDP) was added thereto at 30° C. with stirring and the reaction was carried on for 1 hour. The course of fractionation was followed by passing the reaction product through a column (1×45 cm) of Sephadex G25 equilibrated with 0.1M sodium acetate buffer (pH 4.5) containing 0.1M NaCl to give 0.8 ml fractions, which contained pyridylsulfurized human C3, at the flow rate of 0.5 ml/min. These fractions were pooled and concentrated to the protein concentration of 1 mg/ml by use of a collodion bag while cooling with ice. Then, 1 ml of 0.1M sodium acetate buffer (pH 4.5) containing 0.1M NaCl and 0.1M dithiothreitol was added thereto and the mixture was stirred at 25° C. for 30 minutes to reduce the pyridyldisulfide group introduced into the molecule of human C3. Thereafter, the reaction product was passed through a column (1×45 cm) over Sephadex G 25 equilibrated with 0.1M sodium phosphate buffer containing 0.1M NaCl to obtain 0.8 ml fractions of mercaptyzed human C3 at the flow rate of 0.5 ml/min. These fractions were pooled and concentrated to the protein concentration of 4 mg/ml by use of a collodion bag while cooling with ice.

After the addition of 0.2 ml of 0.1M sodium phosphate buffer containing 0.8 mg of pyridyldisulfurized human IgA prepared according to the same method as Example 1 to the abovementioned concentrate, the mixture was left standing at 40° C. for 24 hours. The reaction product was then put to a column (1.5×45 cm) over ultragel ACA 34 equilibrated with 0.1M sodium phosphate buffer of pH 7.2 to fractionate 1.0 ml fractions at the flow rate of 0.5 ml/min., separating the formed IgA-C3 conjugate from the unreactive protein to give fractions containing lgA-C3 conjugate.

EXAMPLE 5

After a solution was prepared by dissolving 1.0 mg of human C3 in 1.0 ml of 0.1M tris buffer (pH 8.0) containing 0.05M monomethylamine and 0.15M NaCl and shaken at 37° C. for 1 hour, the reaction product was dialyzed overnight against 0.1M tris buffer (pH 7.4) containing 0.15M NaCl to remove unreacted monomethylamine. Then 0.25 ml of pyridyldisurfidized human serum IgA concentrate prepared according to the same method as Example 1 was added to said monomethylamine treated human C3 solution. The mixture was left standing at 4° C. for 24 hours to undergo the reaction. Thus obtained reaction mixture was put to a column (1.5×45 cm) over ultragel ACA 34 equilibrated with 0.1M sodium phosphate buffer of pH 7.2 to fractionate 1 ml-fractions at the flow rate of 0.5 ml/min., thus separating IgA-C3 conjugate from the unreacted proteins. The fractions containing IgA-C3 conjugate were then pooled. The content of IgA component which constitutes the conjugate in the IgA-C3 conjugate solution was determined by the sandwich technique of enzyme immunoassay with the use of the goat anti-(human IgA) antibody fixed solid phase carriers and the horseradish peroxidase labeled $F(ab)_2$ fragment of goat anti-(human IgA) antibody (alpha chain specific) (manufactured by Cappel) and it was found that the yield of IgA-C3 conjugate was 75% based on the starting material of human serum IgA.

EXAMPLE 6

1.5 mg of human serum IgA was dissolved in 1.5 ml of 0.01M phosphate buffer of pH 7.2 containing 0.1M NaCl, and after 60 μl of 30 mM dimethylformamide solution of N-succinimidyl m-(N-maleimido) benzoate (SMB) was added thereto at 25° C. with stirring, the mixture underwent the reaction for 30 minutes. The reaction mixture was then subjected to chromatographic separation of the protein from the low molecular substances on a column (1.5×45 cm) of Sephadex G 25 equilibrated with 0.1M phosphate buffer of pH 6.0 while making 0.8 ml fractions at the flow rate of 0.5 ml/min. to obtain the fractions containing the maleimidyzed human serum IgA.

These fractions were pooled and concentrated to have the protein of 1.5 mg/ml concentration by use of a collodion bag while cooling with ice water.

Thereafter, 0.2 ml of the solution containing mercaptyzed human C3 prepared by the same method as Example 4 to the abovementioned concentrate, and the mixture was left standing at 4° C. for 24 hours. The reaction product was then put to a column (1.5×45 cm) over Ultragel AcA 34 equilibrated with 0.1M phosphate buffer of pH 7.2 to fractionate 1.0 ml fractions at the flow rate of 0.5 ml/min., separating the formed IgA-C$_3$ conjugate from the unreactive proteins to give fractions containing IgA-C3 conjugate.

The content of IgA component which constituted the conjugate in the obtained solution was determined by the same method as Example 1, and it was found that the IgA-C3 conjugate was obtained in a 75% yield.

EXAMPLE 7

A solution of IgG-C3 conjugate was obtained by allowing human IgG to react with mercaptyzed human C3 through the medium of SMB according to the same method as Example 6 by use of human IgG in the place of human serum IgA which was used in Example 6.

The content of IgG component which constituted the conjugate in the obtained solution was determined by the same method as Example 2, and it was found that the IgG-C3 conjugate was obtained in a 75% yield.

EXAMPLE 8

Balls (size 6.5 mm) made of polystyrene were thoroughly washed and immersed in a 0.01M sodium phosphate buffer (pH 7.2) containing 0.85% NaCl which had goat anti-(human C3)-$F(ab')_2$ of 50 μg/ml concentration. The polystyrene balls were left standing in the buffer at 4° C. for 3 days to have anti-(human C3)-$F(ab')_2$ fixed thereto. Each of these polystyrene balls fixed with anti-(human C3)-$F(ab')_2$ was placed in the respective test tubes made of glass. The test tubes were then filled with 0.5 ml of a dilution prepared by diluting each solution, which contained the respective amounts of 50 μg/ml, 25 μg/ml, 10 μg/ml, and 5 μg/ml, and 1 μg/ml of IgA-C3b conjugate obtained in Example 1, up to 200 times with 0.01M sodium phosphate buffer (pH 7.2) containing 0.5% bovine serum albumin (BSA) and 0.85% NaCl and left standing at 30° C. for 2 hours to effect the reaction. Thereafter, the solutions in the test tubes were sucked off and both the test tubes and polystyrene balls were thoroughly washed with 0.01M sodium phosphate buffer (pH 7.2). 0.5 ml of a 1/10,000 dilution, which was prepared by diluting a solution of horseradish peroxidase labeled $F(ab)_2$ fragment of goat anti-(human IgA) antibody (alpha chain specific)-(manufac. by Cappel) with 0.01M sodium phosphate buffer (pH 7.2) containing 0.5% BSA and 0.85% NaCl, was put in the test tubes and they were then left standing at 30° C. for 2 hours. Then the solutions in the respective test tubes were sucked off and the test tubes and polystyrene balls were thoroughly washed with 0.01M sodium phosphate buffer (pH 7.2). Thereafter, 0.5 ml of 0.1M phosphatecitrate buffer (pH 4.5) containing 0.05% 2,2'-azinodi-3-ethylbenzthiazoline-6-sulfonic acid (ABTS) and 0.003% hydrogen peroxide was put in the respective test tubes and left standing at 30° C. for a period of 30 minutes to effect the reaction. Towards the end of this period, 1 ml of 0.2M oxalic acid aqueous solution was added to each test tube to stop the enzyme reaction.

The absorbances at the wavelength of 420 nm of the solutions thus obtained were measured with the use of a spectophotometer. When the obtained results were plotted against the concentration of the standard material, a standard curve showing a good concentration dependence was obtained (FIG. 1). When the concentrations of immune complexes of IgA type in the sera of ordinary healthy persons and of patients with vasculitis were measured with the use of this standard curve, it was observed that the values of immune complexes of IgA type obtained from the group of patients were significantly higher than those obtained from the group of ordinary healthy persons.

EXAMPLE 9

After the polystyrene balls (size 6.5 mmφ) were thoroughly washed, they were immersed in 1/5 VBS (pH 9.5) of 0.02% NaN₃ content having conglutinin, which was isolated and refined according to the method of Eisenberg et al. (Journal of Immunology, vol. 118, p. 1428, (1977)), at the concentration of 5 μg/ml. The device was left standing at 4° C. for 2 days to have the polystyrene balls fixed with conglutinin. The polystyrene balls thus fixed with conglutinin were then left immersed in 1/5 VBS²⁺ of 0.5% BSA content at 4° C. for 24 hours. Thereafter, the polystyrene balls were thoroughly washed and a standard curve of lgA-C3b conjugate was prepared according to the same method as Example 8. This standard curve was found to have a good concentration dependence (FIG. 1).

Note: 1/5 VBS²⁺——10.19 of sodium diethylbarbituric acid and 83 g of NaCl are dissolved in distilled water to make an amount of 1500 ml. After the solution is adjusted to a pH of 7.3 with 1 NHCl, distilled water is added thereto to give a total amount of 2000 ml. Distilled water is added to 1200 ml of thus obtained solution, 150 ml of 0.03M CaCl₂, and 150 ml of 0.1M MgCl₂ to
give an amount of 30 l.

EXAMPLE 10

Figure 2:
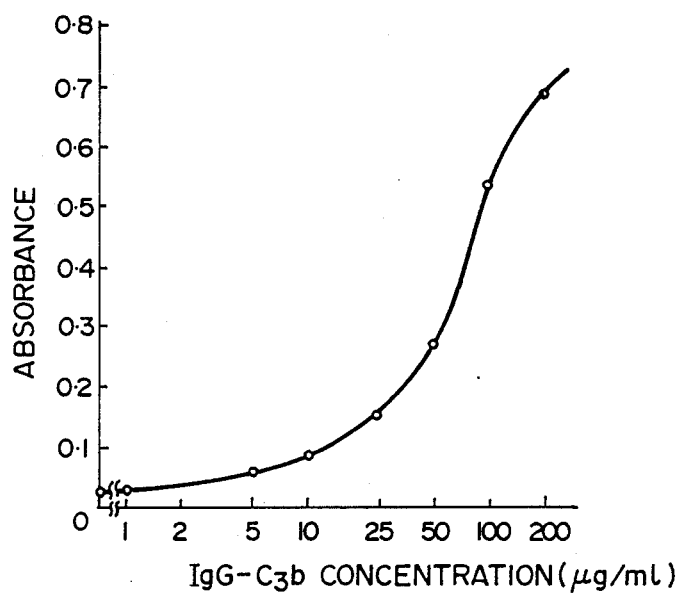
FIG. 2 shows a standard curve prepared by use of IgG-C3b conjugate for determining immune complex of IgG type by enzyme immunoassay.

A standard curve was prepared according to the same method as Example 8, by use of IgG-C3b conjugate prepared in Example 2 in the place of IgA-C3b conjugate which was used as the standard agent in Example 8 and by use of horseradish peroxidase labeled F(ab)₂ fragment of goat anti(human IgG) antibody (gamma hair specific)(manufac. by Cappel) in the place of horseradish peroxidase labeled goat anti-(human IgA) antibody, with the content of IgG-C3b conjugate adjusted to be in the range of 1 μg/ml to 100 μg/ml. It was found that the obtained standard curve showed a good concentration dependence (FIG. 2). When the concentrations of immune complex of IgG type in the sera of healthy persons and of patients with autoimmune diseases such as SLE, etc. were measured with the use of this standard curve, it was observed that the values of immune complex of IgG type were higher with the group of patients than with the group of healthy persons.

EXAMPLE 11

Figure 3:
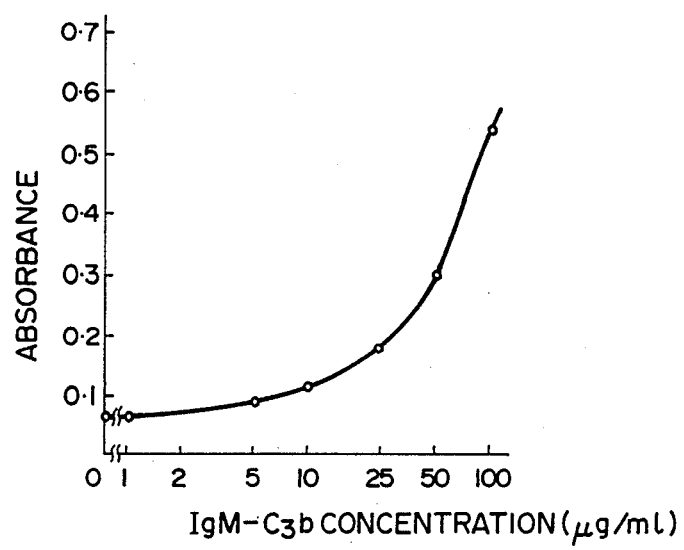
FIG. 3 shows a standard curve prepared by use of IgM-C3b conjugate for determing immune complex of IgM type by enzyme immunoassay.

When a standard curve for IgM-C3b conjugate was prepared according to the same method as Example 8, except for the use of IgM-C3b conjugate prepared in Example 3 instead of IgA-C3b conjugated which was used as the standard agent in Example 8 and the use of horseradish peroxidase labeled F(ab)₂ fragment of goat anti-(human IgM) antibody (gamma hair specific)- (manufac. by Cappel) instead of horseradish peroxidase labeled F(ab)₂ fragment of goat (human IgA) antibody, (alpha chain specific), the obtained standard curve showed a good concentration dependence (FIG. 3). It was observed that the measurements of immune complex of IgM type obtained by use of thus prepared standard curve from a group of patients with autoimmune diseases such as SLE, etc. were high as compared with the group of healthy persons.

As explained above in detail, it has been made possible by the present invention to obtain standard materials for immune complex measurement use having the good stability and reproducibility. It has become possible to determine immune complexes with high precision and excellent reproducibility by immunoassay with the use of these standard materials. It may be said that it has been made possible for the first time by use of the present standard materials to determine the concentration of immune complex of IgA type with good reproducibility, for which there have not been any useful standard materials. It has also been made possible to determine immune complexes by classes by changing the classes of immunoglobulins, thus providing methods useful for making a diagnosis and pathologic research of immune diseases.

What is claimed is:

1. A standard material for measuring immune complexes which is prepared by chemically binding immunoglobulin or its F(ab')₂ fragment or Fab' fragment from a non-immunized individual or FC fragment, with a substance selected from the group consisting of C1, C2, C3, C4, C5, C6, C7, C8, C9, C1q, C1v, C1s, C3c, C3d and Sh group containing derivatives of said C1, C2, C3, C4, C5, C6, C7, C8, or C9, through the medium of a bifunctional reagent.

2. The standard material for measuring immune complexes according to claim 1, wherein said immunoglobulin is any one of human immunoglobulin G(IgG), human immunoglobulin M(IgM), or human immunoglobulin A(IgA).

3. The standard material for measuring immune complexes according to claim 1 or claim 2, wherein said substance is C3.

4. The standard material for measuring immune complexes according to claim 1 or claim 2, wherein said substance obtained by chemically generating or introducing an SH group in or into C3.

5. The standard material for measuring immune complexes according to claim 1 wherein said bifunctional reagent is any one of dialdehyde compounds, diisocyanate compounds, diepoxy compounds, bisdiazo compounds, bismaleimide compounds, carbodiimide compounds, N-succinimidyl N-maleimidocarboxylate compounds, or N-succinimidyl pyridyldithio-carboxylate compounds.

6. The standard material for measuring immune complexes according to claim 2, wherein said bifunctional reagent is any one of dialdehyde compounds, diisocyanate compounds, diepoxy compounds, bisdiazo compounds, bismaleimide compounds, carbodiimide compounds, N-succinimidyl N-maleimido-carboxylate compounds, or N-succinimidyl pyridyldithio-carboxylate compounds.

7. The standard material for measuring immune complexes according to claim 3, wherein said bifunctional reagent is any one of dialdehyde compounds, diisocyanate compounds, diepoxy compounds, bisdiazo compounds, bismaleimide compounds, carbodiimide compounds, N-succinimidyl N-maleimido-carboxylate compounds, or N-succinimidyl pyridyldithio-carboxylate compounds.

8. The standard material for measuring immune complexes according to claim 4, wherein said bifunctional reagent is any one of dialdehyde compounds, diisocyanate compounds, diepoxy compounds, bisdiazo compounds, bismaleimide compounds, carbodiimide compounds, N-succinimidyl N-maleimido-carboxylate compounds, or N-succinimidyl pyridyldithio-carboxylate compounds.

9. In an immunoassay method for quantitatively measuring immune complexes possibly existing in a body fluid with the use of a standard curve, which is prepared for measuring immune complexes, wherein a solid phase carrier fixed with an anti- (human complement) antibody, its F(ab')$_2$, conglutinin (Kg) or combination thereof, is contacted with said body fluid and then the carrier is treated with an enzyme labeled or radiolabeled anti-(human immunoglobulin) antibody and carrying out said measurement by repeating the above technique while substituting a standard material for said body fluid to prepare said standard curve, wherein the improvement comprises using as a standard material for the preparation of said standard curve a material which is prepared by chemically binding immunoglobulin or its F(ab')$_2$, Fab' or Fc fragment with a substance selected from the group consisting of C1, C2, C3, C4, C5, C6, C7, C8, C9, C1q, C1v, C1s, C3b, C3c, C3d and SH group containing derivatives of said C1, C2, C3, C4, C5, C6, C7, C8, or C9, through the medium of a bifunctional reagent.

10. The method as claimed in claim 9, wherein said enzymelabeled or radiolabeled anti-(human immunoglobulin) antibody is a heavy chain-specific antibody.

* * * * *